US011432847B2

(12) United States Patent
Hendler et al.

(10) Patent No.: US 11,432,847 B2
(45) Date of Patent: *Sep. 6, 2022

(54) PERSONAL CARE APPLIANCE

(71) Applicant: MICHAEL TODD BEAUTY LP, Port St. Lucie, FL (US)

(72) Inventors: Lewis Hendler, Rydal, PA (US); Nengfei Xu, Zhejiang Province (CN); Xushan Zhan, Zhejiang Province (CN)

(73) Assignee: MICHAEL TODD BEAUTY LP, Port St. Lucie, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/108,563

(22) Filed: Aug. 22, 2018

(65) Prior Publication Data
US 2018/0353211 A1  Dec. 13, 2018

Related U.S. Application Data

(63) Continuation of application No. 15/073,697, filed on Mar. 18, 2016, now Pat. No. 10,058,351.
(Continued)

(51) Int. Cl.
*A61B 17/54* (2006.01)
*A46B 13/02* (2006.01)
(Continued)

(52) U.S. Cl.
CPC .............. *A61B 17/54* (2013.01); *A46B 13/02* (2013.01); *A46B 13/008* (2013.01); *A46B 2200/102* (2013.01); *A46B 2200/104* (2013.01); *A61B 2017/00398* (2013.01); *A61B 2017/00734* (2013.01); *A61B 2017/00747* (2013.01); *A61B 2017/00752* (2013.01);
(Continued)

(58) Field of Classification Search
CPC .......... A61B 17/54; A61B 2017/00398; A61B 2017/00734; A61B 2017/00747; A61B 2017/00752; A61B 2017/00761; A61B 2017/320004; A61B 2017/320012; A46B 13/02; A46B 13/008; A46B 2200/102; A46B 2200/104
See application file for complete search history.

(56) References Cited

U.S. PATENT DOCUMENTS 3,030,967 A   4/1962   Peyron
3,500,080 A   3/1970   Bey
(Continued)

FOREIGN PATENT DOCUMENTS

WO   97/22325   6/1997
WO   03/096860   11/2003

*Primary Examiner* — Richard G Louis
(74) *Attorney, Agent, or Firm* — Philip E. Levy; Eckert Seamans Cherin & Mellott, LLC

(57) ABSTRACT

A personal care appliance includes a housing, a drive assembly provided in the housing, and a workpiece member. The drive assembly includes a stator and an armature adjacent the stator, wherein the stator, when energized, is structured to cause the armature to oscillate back and forth. The personal care appliance further includes a mounting assembly having a pivot arm having a shaft member and first and second mounting members. The workpiece member is coupled to the first end portion of the shaft member such that oscillation of the armature causes the workpiece member to oscillate relative to the housing.

22 Claims, 10 Drawing Sheets

Related U.S. Application Data

(60) Provisional application No. 62/196,006, filed on Jul. 23, 2015, provisional application No. 62/135,198, filed on Mar. 19, 2015.

(51) Int. Cl.
  *A46B 13/00* (2006.01)
  *A61B 17/00* (2006.01)
  *A61B 17/32* (2006.01)

(52) U.S. Cl.
  CPC ............... *A61B 2017/00761* (2013.01); *A61B 2017/320004* (2013.01); *A61B 2017/320012* (2013.01)

(56) References Cited

U.S. PATENT DOCUMENTS

| | | | |
|---|---|---|---|
| 3,699,952 A | 10/1972 | Waters et al. | |
| 3,906,940 A | 9/1975 | Kawada | |
| 3,968,789 A * | 7/1976 | Simoncini | A46B 13/04 601/95 |
| 4,027,348 A | 6/1977 | Flowers et al. | |
| 4,040,414 A | 8/1977 | Suroff | |
| 4,158,246 A | 6/1979 | Meadows et al. | |
| 4,203,431 A | 5/1980 | Abura et al. | |
| 4,281,987 A | 8/1981 | Kleesattel | |
| 4,670,931 A | 6/1987 | Abbassi | |
| 4,724,563 A | 2/1988 | Fry et al. | |
| 4,919,117 A | 4/1990 | Muchisky et al. | |
| 5,012,797 A | 5/1991 | Liang et al. | |
| 5,186,627 A | 2/1993 | Amit et al. | |
| 5,189,751 A | 3/1993 | Giuliani et al. | |
| 5,467,495 A | 11/1995 | Boland et al. | |
| 5,544,282 A | 8/1996 | Chen et al. | |
| 5,624,416 A | 4/1997 | Schatz | |
| 5,687,442 A | 11/1997 | McLain | |
| 5,697,115 A | 12/1997 | Sciarra et al. | |
| 5,891,063 A | 4/1999 | Vigil | |
| 6,021,538 A | 2/2000 | Kressner et al. | |
| 6,032,313 A * | 3/2000 | Tsang | A46B 13/02 15/21.1 |
| 6,108,847 A | 8/2000 | Cueman et al. | |
| 6,170,108 B1 | 1/2001 | Knight | |
| 6,253,405 B1 | 7/2001 | Gutelius et al. | |
| 6,363,565 B1 | 4/2002 | Paffrath | |
| 6,471,712 B2 | 10/2002 | Burres | |
| 6,564,940 B2 | 5/2003 | Blaustein et al. | |
| 6,569,170 B1 | 5/2003 | Kellogg | |
| 6,575,924 B2 | 6/2003 | Wevers et al. | |
| 6,645,184 B1 | 11/2003 | Zelickson et al. | |
| D500,209 S | 12/2004 | Kellogg | |
| 6,836,917 B2 | 1/2005 | Blaustein et al. | |
| 6,845,537 B2 | 1/2005 | Wong | |
| 7,157,816 B2 | 1/2007 | Pilcher et al. | |
| D549,964 S | 9/2007 | Roth et al. | |
| 7,320,691 B2 | 1/2008 | Pilcher et al. | |
| 7,386,906 B2 | 6/2008 | Roth et al. | |
| 7,469,703 B2 | 12/2008 | Rance et al. | |
| 7,786,626 B2 | 8/2010 | Reishus et al. | |
| D683,139 S | 5/2013 | Chikos et al. | |
| 8,469,909 B2 | 6/2013 | Pilcher et al. | |
| 8,484,788 B2 | 7/2013 | Brewer et al. | |
| 8,740,917 B2 | 6/2014 | Pilcher et al. | |
| 2002/0049199 A1 | 4/2002 | Klopotek | |
| 2002/0049399 A1 | 4/2002 | Stampf | |
| 2003/0125754 A1 | 7/2003 | Davis et al. | |
| 2004/0010222 A1 * | 1/2004 | Nunomura | A61B 17/54 604/22 |
| 2005/0280319 A1 * | 12/2005 | Pilcher | H02K 33/16 310/36 |
| 2007/0198031 A1 | 8/2007 | Kellogg | |
| 2008/0106156 A1 | 5/2008 | Reishus et al. | |
| 2009/0177125 A1 | 7/2009 | Pilcher et al. | |
| 2009/0198262 A1 | 8/2009 | Rosenblood et al. | |
| 2009/0306577 A1 | 12/2009 | Akridge et al. | |
| 2012/0159795 A1 | 6/2012 | Walmsley | |
| 2014/0007362 A1 * | 1/2014 | Park | A47K 7/04 318/400.34 |

* cited by examiner

FIRST LATERAL MAX POSITION-NO PAUSE BEFORE MOVING IN OPPOSITE DIRECTION

FIRST LATERAL MAX POSITION-NO PAUSE BEFORE MOVING IN OPPOSITE DIRECTION

FIRST LATERAL MAX POSITION-PAUSE BEFORE MOVING IN OPPOSITE DIRECTION

FIRST LATERAL MAX POSITION-PAUSE BEFORE MOVING IN OPPOSITE DIRECTION

PERSONAL CARE APPLIANCE

CROSS-REFERENCE TO RELATED APPLICATIONS

This application is a Continuation of U.S. patent application Ser. No. 15/073,697, filed on Mar. 18, 2016, entitled "Personal Care Appliance," which claims priority under 35 U.S.C. § 119(e) from U.S. Provisional Application No. 62/135,198, filed on Mar. 19, 2015, entitled "Personal Care Appliance," and U.S. Provisional Application No. 62/196,006, filed on Jul. 23, 2015, entitled "Personal Care Appliance," the contents of which are incorporated herein by reference.

BACKGROUND OF THE INVENTION

1. Field of the Invention

The present invention pertains to personal care appliances, such as a power skin care brush, that are used to care for, clean and otherwise treat skin and hair, and, in particular, to a portable, electrically driven, handheld device that may be used to care for, clean and otherwise treat skin and hair.

2. Description of the Related Art

Handheld personal care appliances used to care for, clean or otherwise treat the skin or hair (e.g., to clean, massage and/or apply creams, cleansing solutions or other substances to the skin or hair) are known and have gained increasing popularity. Such devices are most often used to provide daily hygienic skin care, in particular care for the facial skin. These devices usually include a small handheld casing having an internal motor and a self-contained power source (such as a battery) for producing a particular movement/action of a workpiece (e.g., a brush or pad), which in turn produces desired functional results. Examples of such appliances include power skin brushes and power toothbrushes, among others. Such personal care appliances have motor arrangements which produce either rotational movement or oscillating (back and forth) movement.

While many such devices are known, there is room for improvement in the field of personal care appliances such as handheld skin and hair treatment devices. Hence, it is desirable to have a personal care appliance having a drive assembly which is powerful (stronger and faster), energy efficient, quiet and durable.

SUMMARY OF THE INVENTION

In one embodiment, a personal care appliance is provided that includes a housing, a drive assembly provided in the housing, and a workpiece member. The drive assembly includes a stator, and an armature adjacent the stator, wherein the stator, when energized, is structured to cause the armature to oscillate back and forth. The personal care appliance also includes a first mounting member secured to the housing, the first mounting member having a first hole extending through the first mounting member and forming part of a first bearing member. The personal care appliance further includes a pivot arm member including a first arm, a second arm, and a shaft member provided between the first arm and the second arm. The shaft member has a first end portion and a second end portion, wherein a first end of the first arm is coupled to the armature assembly and a second end of the first arm is coupled to a first side of the shaft member, wherein a first end of the second arm is coupled to a second side of the shaft member opposite the first side of the shaft member, and wherein a second end of the second arm is coupled the first mounting member. Also included is a second mounting member secured to the first mounting member, the second mounting member having a second hole aligned with the first hole and extending through the second mounting member and forming part of a second bearing member, wherein the first end portion of the shaft member is received through the first hole and the second end portion of the shaft member is received through the second hole. The workpiece member is coupled to the first end portion of the shaft member such that oscillation of the armature causes the workpiece member to oscillate relative to the housing.

In another embodiment, a personal care appliance is provided that includes a housing, a drive assembly provided in the housing, the drive assembly including a stator and an armature adjacent the stator, wherein the stator, when energized, is structured to cause the armature to oscillate back and forth. The personal care appliance further includes a workpiece member coupled to drive assembly such that oscillation of the armature causes the workpiece member to oscillate relative to the housing, and control electronics structured to control operation of the stator and armature such that the armature is caused to oscillate back and forth in a pulse mode wherein the armature is caused to move back and forth between a first lateral maximum position and a second lateral maximum position with a pause at each of the first lateral maximum position and the second lateral maximum position before initiating movement in an opposite direction.

In still another embodiment, a brush head assembly structured to be selectively attachable to drive assembly of a personal care appliance is provided. The brush head assembly includes a base member having a front side and a rear side, a plurality of bristles arranged on and extending from the front side, and a hexagonal female attachment structure provided on the rear side and structured to receive a hexagonal male member provided as part of the drive assembly.

DETAILED DESCRIPTION OF EXEMPLARY EMBODIMENTS

Figure 1:
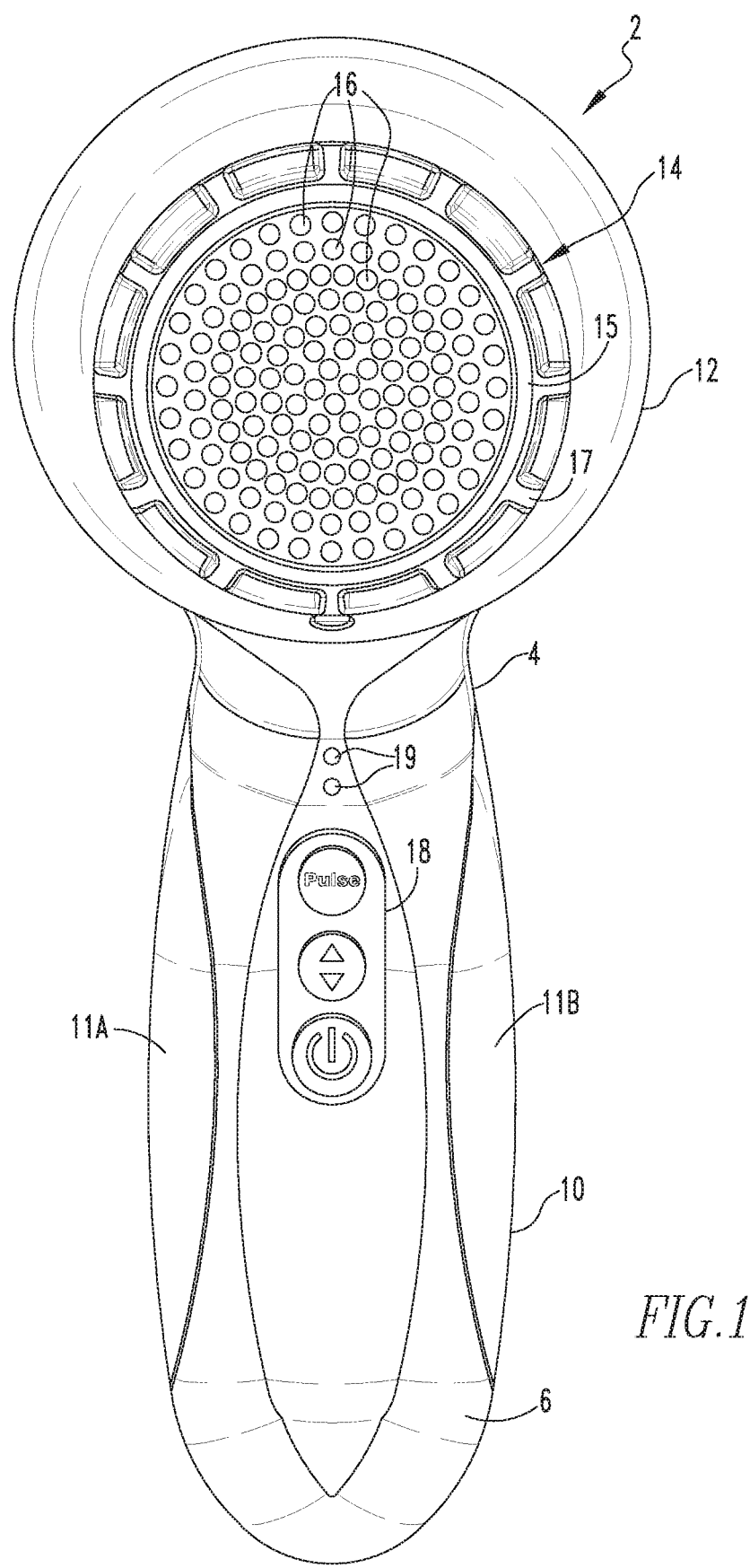
FIG. 1 is a front elevational view of a handheld personal care appliance according to an exemplary embodiment of the present invention.

As used herein, the singular form of "a", "an", and "the" include plural references unless the context clearly dictates otherwise.

As used herein, the statement that two or more parts or elements are "coupled" shall mean that the parts are joined or operate together either directly or indirectly, i.e., through one or more intermediate parts or elements, so long as a link occurs.

As used herein, "directly coupled" means that two elements are directly in contact with each other.

As used herein, "fixedly coupled" or "fixed" means that two elements are coupled so as to move as one while maintaining a constant orientation relative to each other.

As used herein, the word "unitary" means a part is created as a single piece or unit. That is, a part that includes pieces that are created separately and then coupled together as a unit is not a "unitary" part or body.

As employed herein, the statement that two or more parts or elements "engage" one another shall mean that the parts exert a force against one another either directly or through one or more intermediate parts or elements.

As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2:
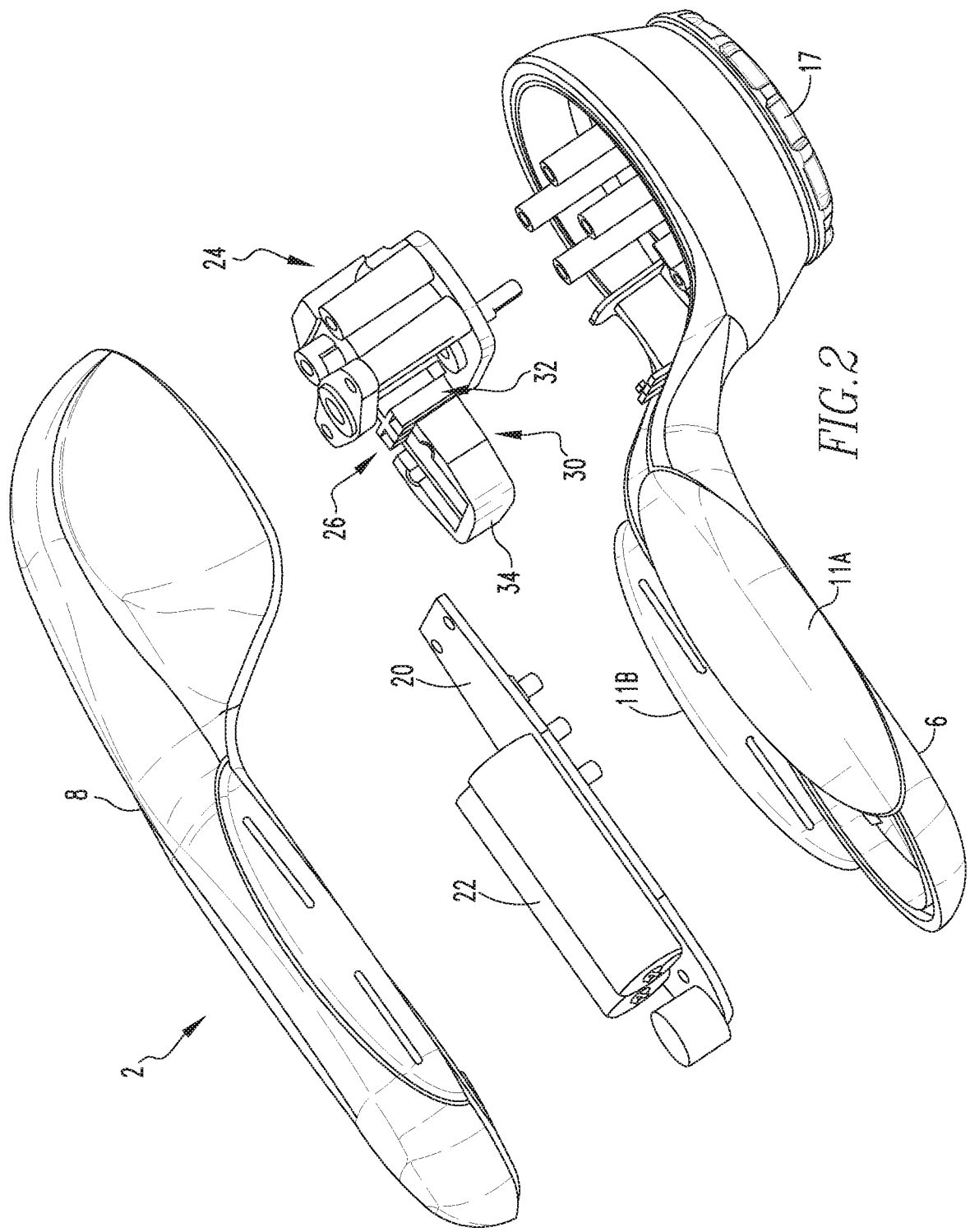
FIG. 2 is a rear isometric exploded view.
Figure 3:
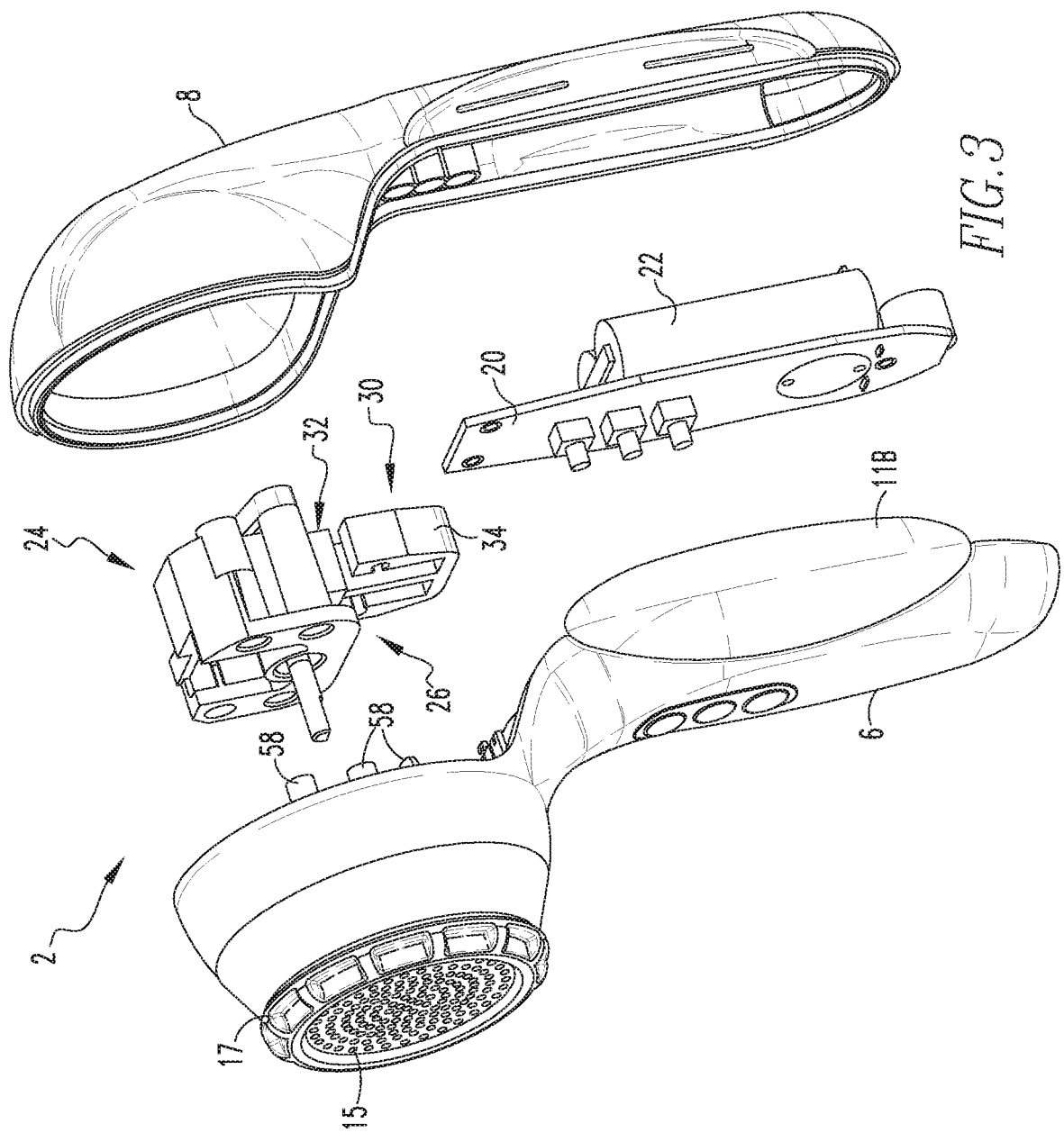
FIG. 3 is a front isometric exploded view of the handheld personal care appliance of FIG. 1.

FIG. 1 is a front elevational view, FIG. 2 is a rear isometric exploded view, and FIG. 3 is a front isometric exploded view of a handheld personal care appliance 2 according to an exemplary embodiment of the present invention. In the illustrated embodiment, personal care appliance 2 includes a two-part main housing 4 having a first (front) portion 6 and a second (rear) portion 8 coupled to the first portion 6. Also, main housing 4 includes a handle portion 10 provided at a first end thereof and structured to enable the user to grip and hold personal care appliance 2, and an attachment portion 12 provided at a second end thereof and structured to mount and hold a workpiece member in a manner that permits the workpiece member to be oscillated for use in skin and/or hair care, cleaning and treatment as described in detail herein. In addition, in the exemplary embodiment, handle portion 10 is provided with non-slip overlay portions 11A and 11B that are coupled to the surface of handle portion 10. Non-slip overlay portions 11A and 11B are made of a material, such as rubber, and, in the exemplary embodiment, include a plurality of protruding members (not shown) (e.g., bumps) to aid in securely gripping and holding personal care appliance 2.

In the illustrated, non-limiting embodiment, workpiece member is a circular brush head assembly 14 having a base member 15, a plurality of bristles 16 (shown only in FIG. 1 and not in FIGS. 2 and 3) arranged on and extending from base member 15 in a circular pattern, and a locking ring 17 structured to secure brush head assembly 14 in place. It will be appreciated, however, that other types of workpiece members may be used in place of bush head assembly 14, such as, without limitation, a pad member assembly or massage head assembly.

Because of the presence of microbes such as bacteria and fungi in all walks of human life, there is a constant interaction between microbes and humans. This is especially so in the workpiece member, where skin cells left on the bristles 16 from the exfoliating effects of the brush head or other workpiece member provide a food source for microorganisms, which when combined with moisture and light, provide a breeding ground for the growth of mold, mildew and fungus, as well as, microbes, pathogens and bacteria, such as *E. coli* and Staph, and other microorganisms. Tests have shown that on unprotected surfaces, bacteria can double in number every 20 minutes.

Thus, in one non-limiting exemplary embodiment, the components of the workpiece member including, without limitation, the bristles 16, are made with active ingredients during the manufacturing stage that are both (i) safe for use on the skin, and (ii) resist and inhibit the growth of mold, mildew, fungus and/or bacteria on the workpiece member, keeping the workpiece member cleaner and healthier for a longer period of time. By helping prevent the growth of microorganisms, stain and odor control is also achieved.

Such active ingredients may include, for example and without limitation, silver ion technology (wherein silver ions are incorporated as an additive at the time of manufacture, or applied as a coating after manufacture), which forms a safe protective antimicrobial surface to resist and inhibit bacterial growth by up to 99.94%. Such active ingredients may further include, without limitation, essential plant oils (e.g., cinnamon oil, clove oil, eucalyptus oil, oregano oil, lavender oil, leleshwa oil, lemon oil, lemon myrtle oil, mint oil, neem oil, nigella sativa (black cumin) oil, peppermint oil, sandalwood oil, ironwort oil, tea tree oil, and thyme oil), and essential minerals, or bacteria resistant polymers (e.g., a polymer that reduces the ability of pathogenic bacteria to attach to the polymer).

An actuator mechanism 18 including a number of buttons is provided on handle portion 10 for controlling the operation of personal care appliance 2 (i.e., controlling the starting, stopping and/or speed of the movement of brush head assembly 14). In addition, handle portion 10 also includes a number of indicator lights 19 for indicating various modes of operation of personal care appliance 2.

As noted elsewhere herein, FIG. 2 is a rear isometric exploded view and FIG. 3 is a front isometric exploded view of personal care appliance 2. FIGS. 2 and 3 allow the internal components of personal care appliance 2 to be readily viewed. As seen in FIGS. 2 and 3, a main circuit board 20 is mounted and held within handle portion 10 of main housing 4. Main circuit board 20 includes the control electronics (including a processing device such as, without limitation, a microprocessor or a microcontroller) which control the operation of personal care appliance 2. A rechargeable battery 22 is coupled to main circuit board 20 and is adapted to provide power for personal care appliance 2.

Figure 4:
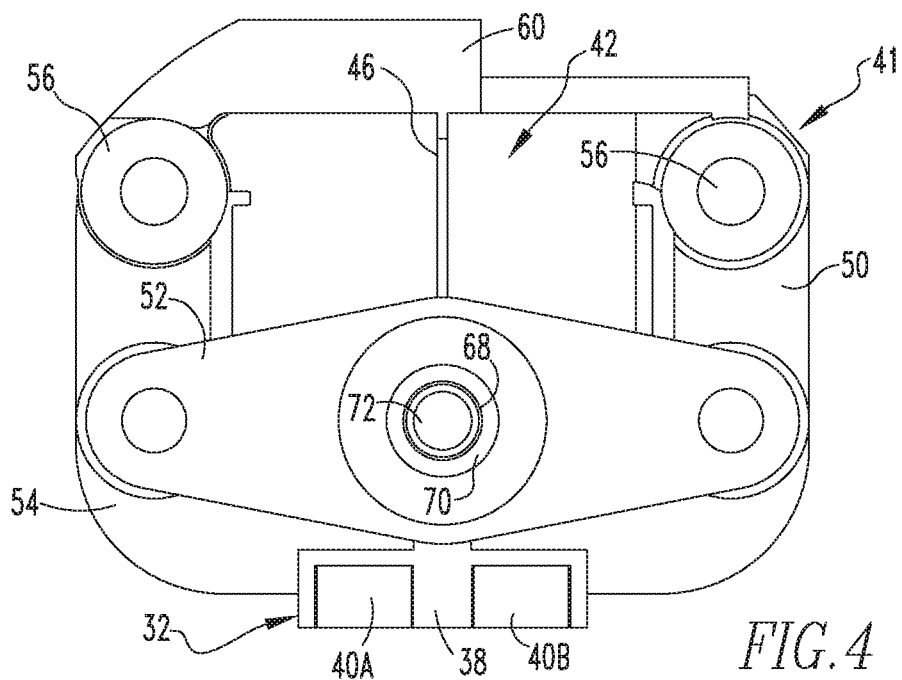
FIG. 4 is a top plan view.

In addition, as seen in FIGS. 2 and 3, a drive assembly 24 is mounted and held within attachment portion 12 of main housing 4. Brush head assembly 14 is structured to be selectively attached to drive assembly 24 so that, as described in more detail below, drive assembly 24 is able to move brush head assembly 14 in an oscillating manner with respect to main housing 4. A pivot assembly 41 (described in detail herein) of drive assembly 24 is shown in FIG. 4 (top plan view), FIG. 5 (top isometric exploded view), and FIG. 6 (bottom isometric exploded view), and, as described below, is the structure that enables brush head assembly 14 to be moved in an oscillating manner by motor 26.

As seen in FIGS. 2 and 3, drive assembly 24 includes an electric motor 26 that is coupled to main circuit board 20 and rechargeable battery 22 by wires (not shown). Motor 26 includes a stator assembly 30 and an armature assembly 32. Stator assembly 30 includes an E-core member 34 having first and second outer legs and a center leg in between the outer legs, and a stator coil (not shown) wrapped around the center leg of E-core member 34. Armature assembly 32 includes a main body portion 38 and first and second magnets 40A, 40B (see FIGS. 4-6) spaced apart from one another and coupled to a first side of main body portion 38. First and second magnets 40A, 40B are oriented such that the poles of first and second magnets 40A, 40B face in opposite directions (e.g., the N pole of magnet 40A faces stator assembly 30 and the S pole of magnet 40B faces stator assembly 30).

Drive assembly 24 further includes a pivot assembly 41 that is structured to be coupled to brush head assembly 14 as described herein to enable brush head assembly 14 to move in an oscillating manner with respect to main housing 4. Pivot assembly 41 includes a pivot arm member 42, a first mounting member 50 and a second mounting member 52. First mounting member 50 is structured to be secured to the interior of attachment portion 12 of main housing 4 by a plurality of screws in order to secure drive assembly 24 in place. In particular, first mounting member 50 includes a base member 54 having four screw cylinders 56 extending upwardly therefrom. Screw cylinders 56 are structured to be fit over and secured to peg members 58 provided as part of attachment portion 12 by four screws (not shown). Base member 54 further includes a mounting arm 60 that is coupled to and extends between the top two of the screw cylinders 56 as shown. Second mounting member 52 is structured to be secured to the bottom two of the screw cylinders 56 of first mounting member 50 to provide further support and stability to drive assembly 24 as it operates as described herein.

Pivot arm member 42 includes a first arm 44, a second arm 46, and a generally cylindrical shaft member 48 provided between first arm 44 and second arm 46 in a manner wherein the longitudinal axis of cylindrical shaft member 48 is perpendicular to the longitudinal axis of both first arm 44 and second arm 46. A first end of the first arm 44 is directly coupled to a second side of main body portion 38 (opposite the first side thereof, i.e., opposite magnets 40A, 40B), and a second end of the first arm 44 is directly coupled to a first side of cylindrical shaft member 48. A first end of second arm 46 is directly coupled to a second side of cylindrical shaft member 48 (opposite the first side of cylindrical shaft member 48), and a second end of second arm 46 is directly coupled to mounting arm 60.

In addition, base member 54 of first mounting member 50 includes a through hole 62 supporting a first disc shaped bearing insert 64 (e.g., made of a thermoplastic elastomer such as thermoplastic rubber) which receives a first end 66 of shaft member 48 therethrough. Thus, through hole 62 and bearing insert 64 function as a first bearing member for shaft member 48. Similarly, second mounting member 52 includes a through hole 68 supporting a second disc shaped bearing insert 70 (e.g., made of a thermoplastic elastomer such as thermoplastic rubber) which receives a second end 72 (opposite first end 66) of shaft member 48 therethrough. Thus, through hole 68 and bearing insert 70 function as a second bearing member for shaft member 48.

In addition, as seen in FIGS. 2 and 3, first end 66 of shaft member 48 that extends through base member 54 is structured to be selectively coupled to brush head assembly 14 through a central aperture provided in attachment portion 12 (first end 66 of shaft member 48 is structured to extend through that central aperture to facilitate selective connection of brush head assembly 14, or a different skin treatment attachment device, thereto). Thus, when assembled, the center of base member 15 of brush head assembly 14 will be aligned directly with the bearing members forming a part of pivot assembly 41.

In operation, when power is provided to motor 26 by rechargeable battery 22, armature assembly 32 will be caused to oscillate back and forth in an arcuate path as a result of the changing magnetic field produced in stator assembly 30 and the interaction of magnets 40A, 40B therewith. As a result, shaft member 48 will be caused to oscillate, which will cause brush head assembly 14, coupled to shaft member 48, to oscillate with respect to main housing 4. A user may then apply the oscillating bush head assembly 14 to different areas of skin and/or hair (e.g., the face, feet, etc.) to provide care and treatment for the skin and/or hair, for example by using the oscillating brush head assembly to apply a cleansing solution or another substance to the user's skin and/or hair.

The bearing members forming a part of pivot assembly 41 as described herein make the oscillation of shaft member 48 and brush head assembly 14 extremely stable and minimize the noise created thereby. The bearing members also ensure that brushhead assembly 14 will oscillate about the middle of attachment portion 12 of main housing 4 with minimum resistance (which helps to reduce waste of power and therefore helps to increase battery life). In addition, second arm 46 coupled to mounting arm 60 enables personal care appliance to 2 operate with increased power has it provides an automatic rebound affect.

In the exemplary embodiment, pivot assembly 41 is made from a zinc alloy material for provided maximum strength.

As will be appreciated, during operation, when armature assembly 32 oscillates, after starting from an initial midpoint, armature assembly 32 will move back and forth between a first lateral (e.g. left) maximum position and an opposite second lateral (e.g. right) maximum position. In the exemplary embodiment, the control electronics of main circuit board 20 are programmed to control operation of personal care appliance 2 such that it is able to operate in at least two modes, the first mode being a "normal" mode (with one or more (preferably multiple) speeds) and the second mode being a "pulse" mode (with one or more (preferably multiple) speeds), each of which is discussed below.

Figure 7:
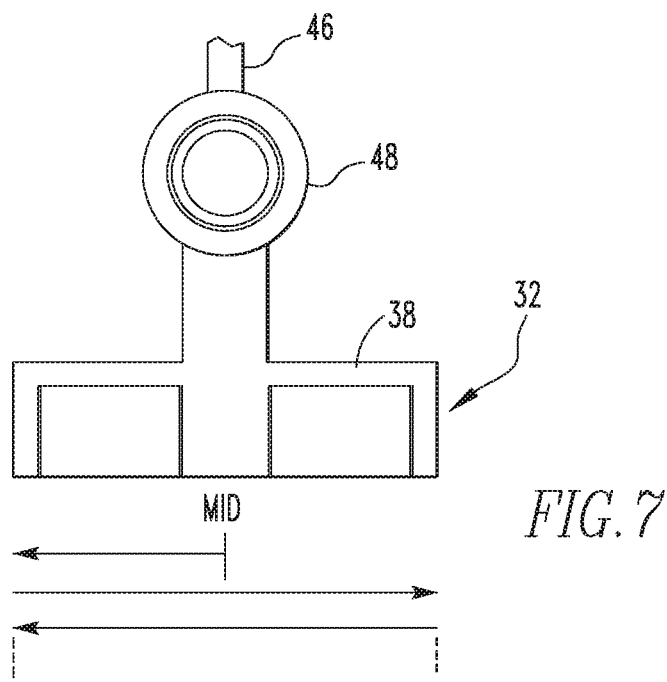
FIG. 7 is a schematic diagram showing operation of the handheld personal care appliance of FIG. 1.

In the "normal" mode of operation, armature assembly 32 is controlled such that, after the initial move from the initial midpoint to the first lateral maximum position, armature assembly 32 moves back and forth between the first lateral maximum position and the second lateral maximum position without pausing at either the first lateral maximum position or the second lateral maximum position before initiating movement in the opposite direction. This "normal" mode of operation is shown schematically in FIG. 7. In other words, operation is as follows: move in first direction, no pause, move in second direction, no pause, move in first direction, no pause, move in second direction, no pause, and so on. In the "normal" mode of operation, a complete "cycle" is thus defined as moving from the first lateral maximum position to the second lateral maximum position and back to the first lateral maximum position. Thus, the timing or "period" of a cycle starts when armature assembly 32 first moves from the first lateral maximum position and ends when armature assembly 32 returns to the first lateral maximum position. In one exemplary embodiment, personal care appliance 2 is controlled to operate in the "normal" mode of operation with selectable speeds of 250 cycles/second, 270 cycles/second, and 280 cycles/second.

Figure 8:
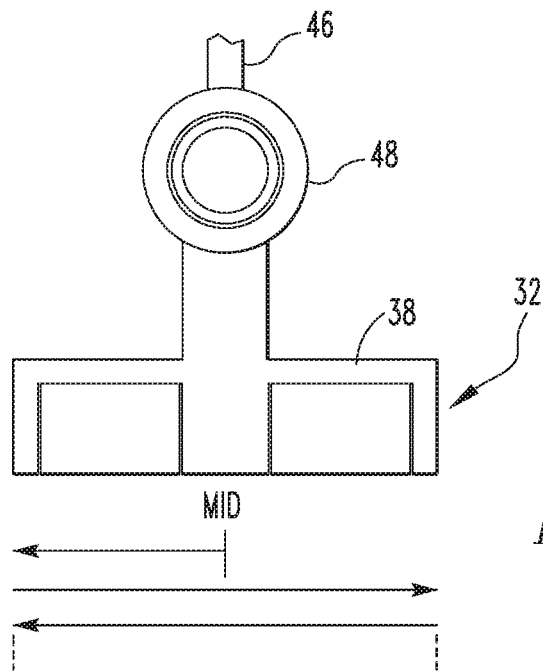
FIG. 8 is a schematic diagram showing operation of the handheld personal care appliance of FIG. 1 in a pulse mode of operation.

In the "pulse" mode of operation, armature assembly 32 is controlled such that, after the initial move from the initial midpoint to the first lateral maximum position, armature assembly 32 moves back and forth between the first lateral maximum position and the second lateral maximum position with a pause (period of rest/no movement) of at least 300 milliseconds at each of the first lateral maximum position and the second lateral maximum position before initiating (by the motor 26) movement in the opposite direction. This "pulse" mode of operation is shown schematically in FIG. 8. In other words, operation is as follows: move in first direction, pause at first lateral maximum position, move in second direction, pause at second lateral maximum position, move in first direction, pause at first lateral maximum position, move in second direction, pause at second lateral maximum position, and so on. In the "pulse" mode of operation, a complete cycle is thus defined as moving from the first lateral maximum position to the second lateral maximum position and back to the first lateral maximum position, including the complete pause at the second lateral position and the first lateral position. Thus, the timing or period of a cycle starts when armature assembly 32 first moves from the first lateral maximum position and ends following the pause when the armature assembly 32 returns to the first lateral maximum position. In one exemplary embodiment, personal care appliance 2 is controlled to operate in the "pulse" mode of operation with selectable speeds of 240 cycles/second, 220 cycles/second, and 200 cycles/second.

In one particular exemplary embodiment, personal care appliance 2 is structured and configured such that personal care appliance 2 will operate for about 45-55 minutes on a single charge and such that only about 2 milliamperes is consumed when personal care appliance 2 is not in use (which prolongs the battery life).

Figure 5:
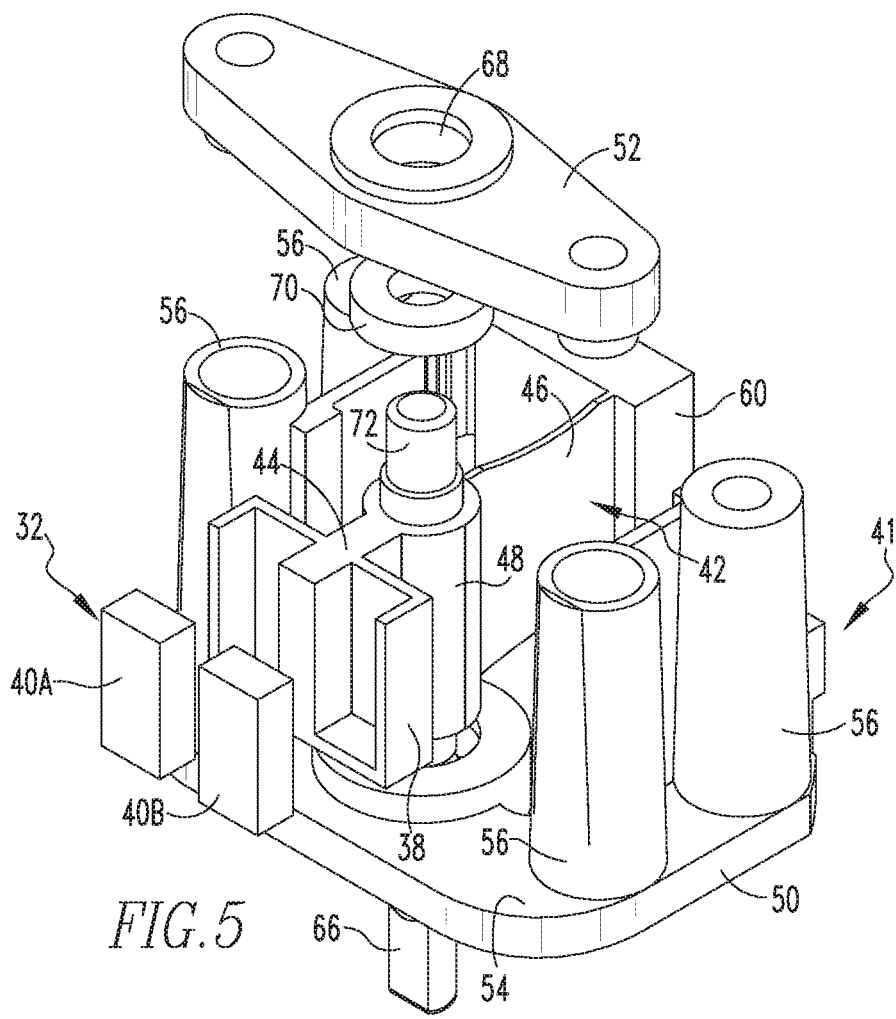
FIG. 5 is a top isometric exploded view.
Figure 6:
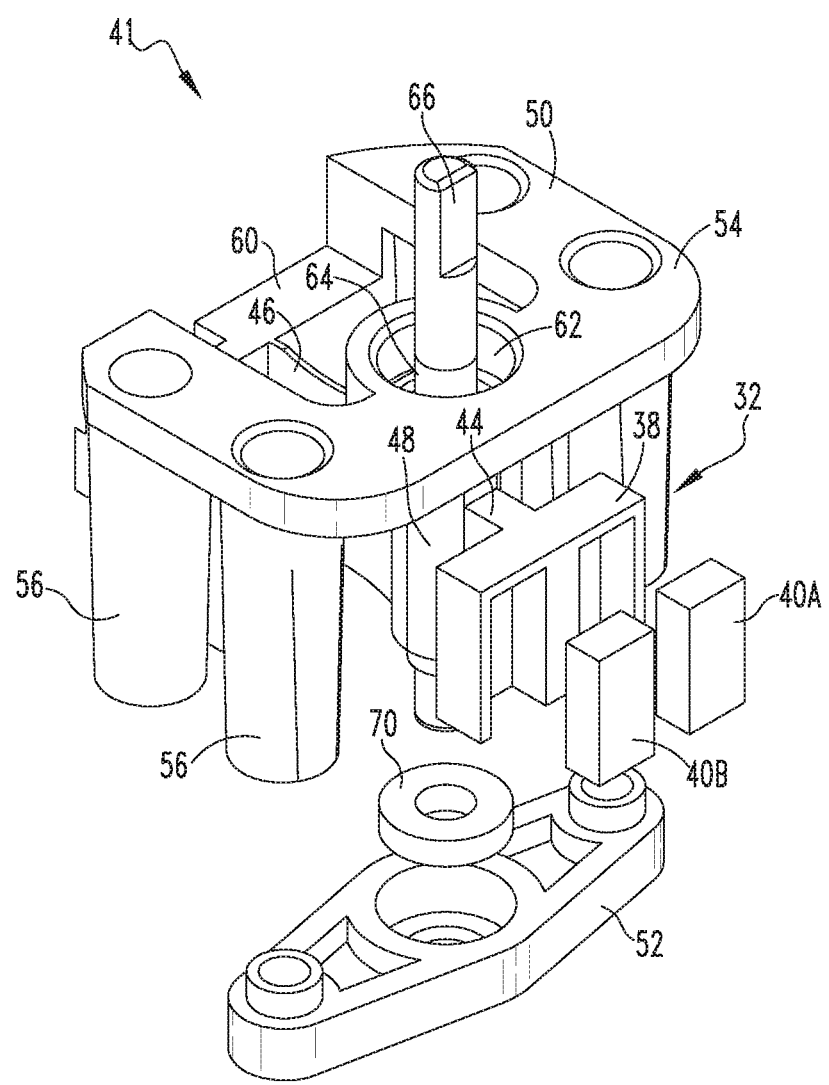
FIG. 6 is a bottom isometric exploded view of a portion of the drive assembly of the handheld personal care appliance of FIG. 1.
Figure 9A:
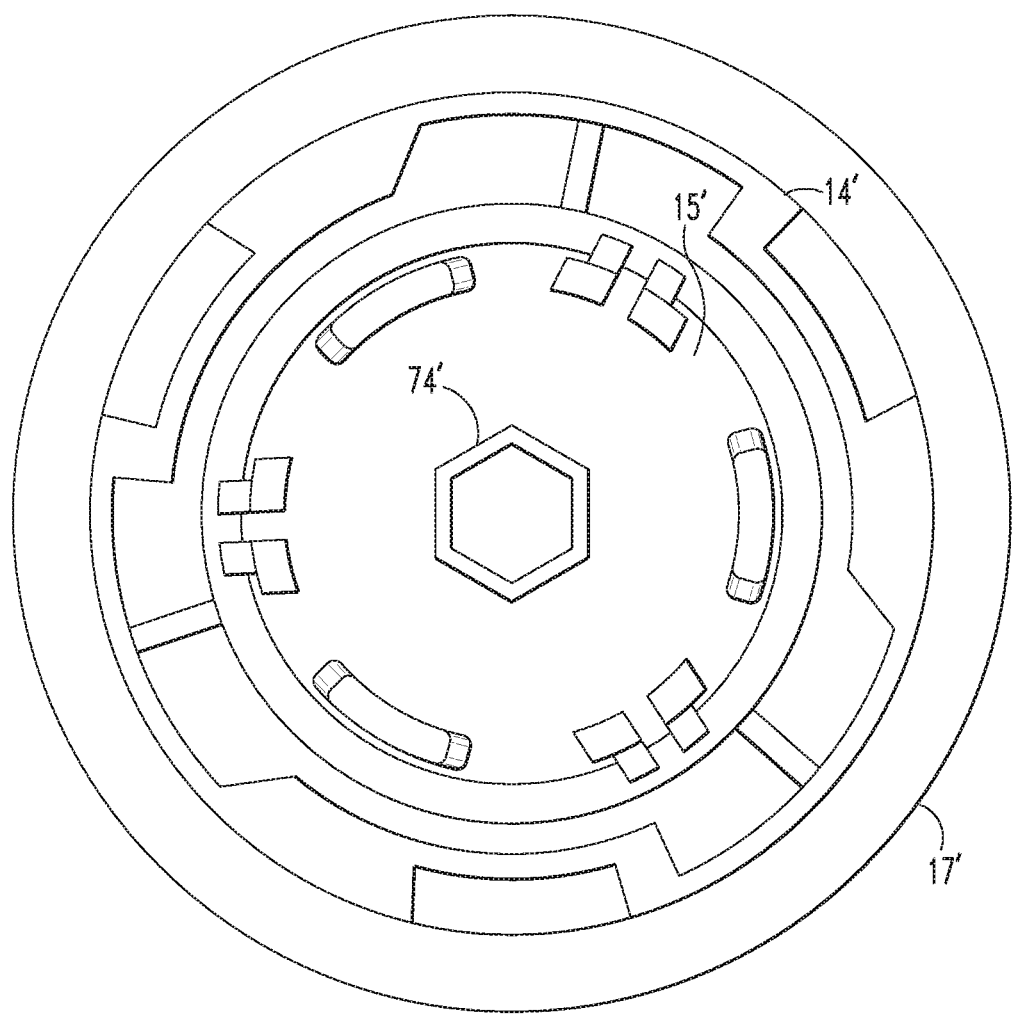
FIG. 9A is a rear view of a brush head assembly according to an alternative embodiment.
Figure 9B:
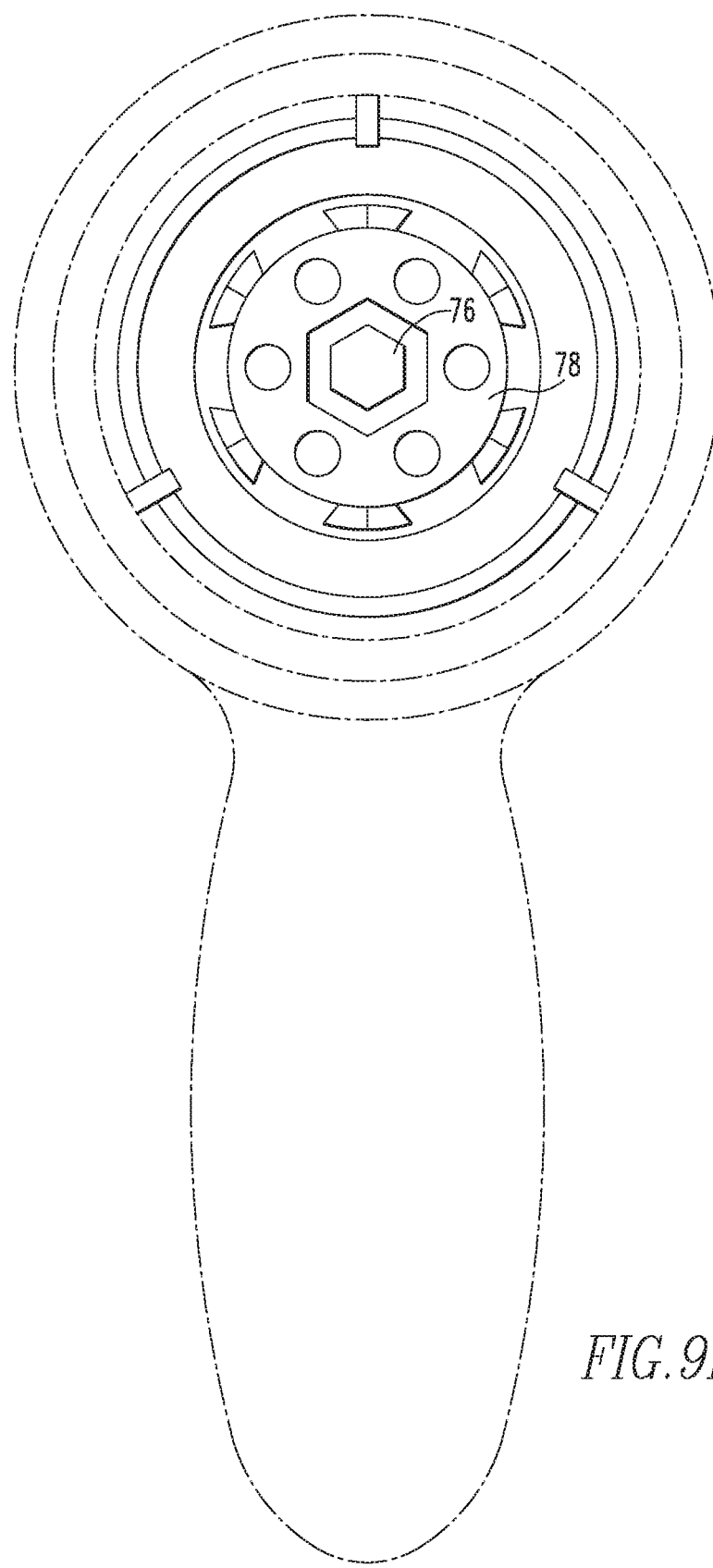
FIG. 9B is a top plan view of a portion of a personal care appliance according to an alternative embodiment.

FIGS. 9A and 9B show an alternative workpiece member in the form of a circular brush head assembly 14' that may be used in place of circular brush head assembly 14. Circular brush head assembly 14' has a base member 15', a plurality of bristles 16 as described herein arranged on and extending from base member 15' in a circular pattern, and a locking ring 17 as described herein structured to secure brush head assembly 14' in place. FIG. 9A is a rear view of circular brush head assembly 14'. As seen in FIG. 9A, base member 15' includes a female attachment structure 74 that comprises a hexagonal member having six outwardly extending walls that is structured to receive a male hexagonal end member 76 of a mounting member 78 that is attached to end 66 of shaft member 48 (FIG. 5). Thus, the configuration shown in FIGS. 9A and 9B ensures that only workpieces that have a female attachment structure 74 can be attached to shaft member 48 and used with the brush configuration described herein.

Figure 10A:
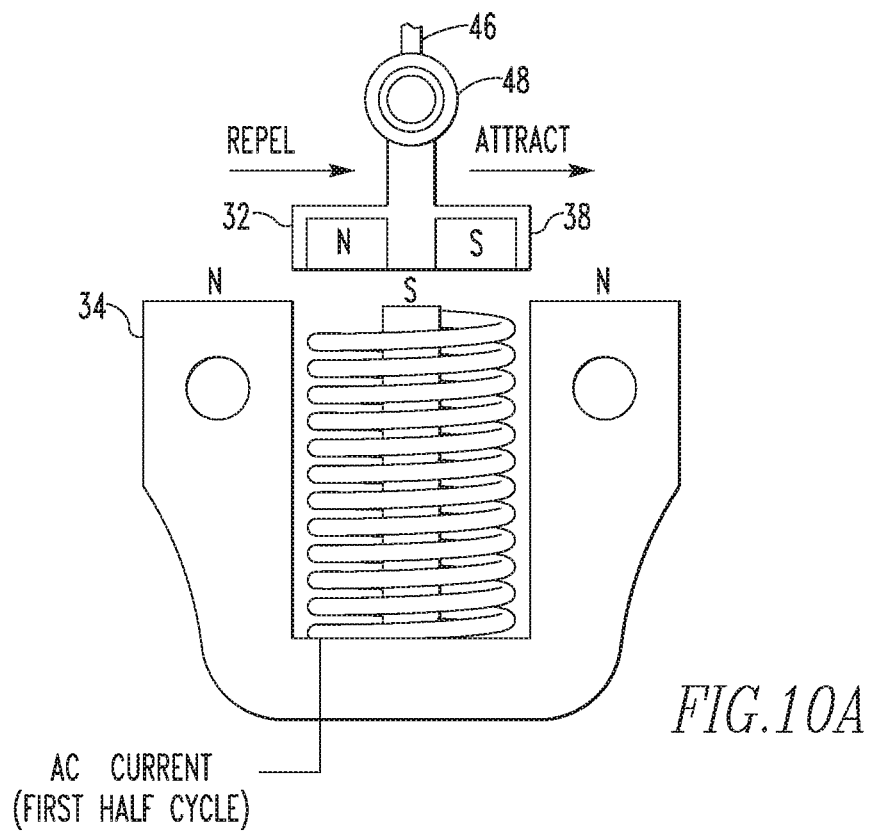
FIGS. 10A and 10B are schematic diagrams showing operation of handheld personal care appliance of FIG. 1 in an alternative mode of operation.
Figure 10B:
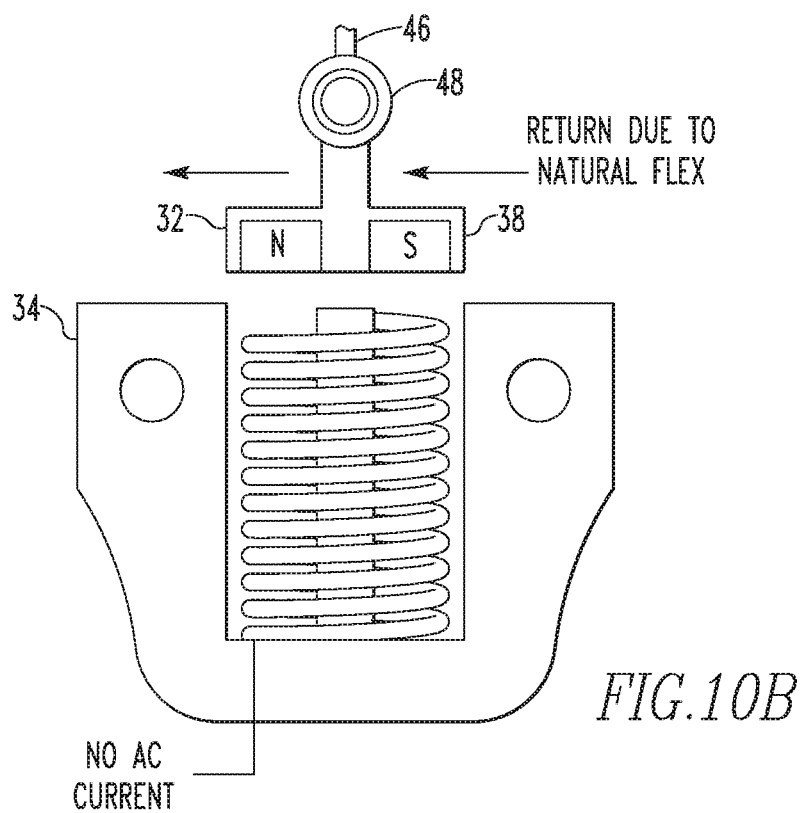
Figure 11A:
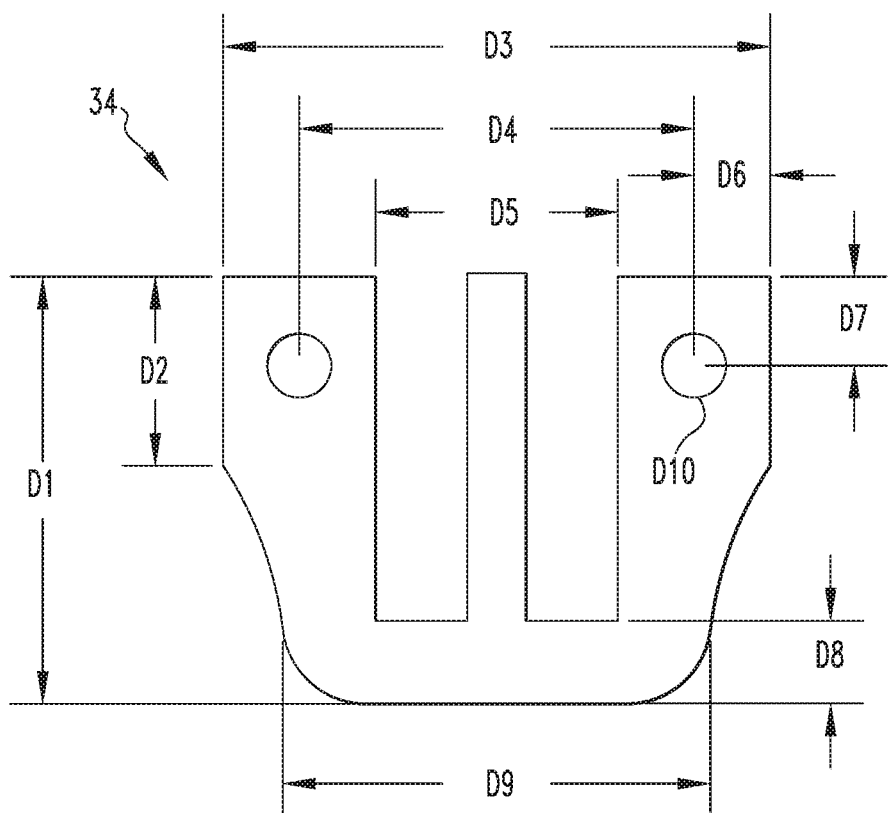
FIGS. 11A and 11B are top plan and bottom elevational views of an E-core member according to one embodiment.
Figure 11B:
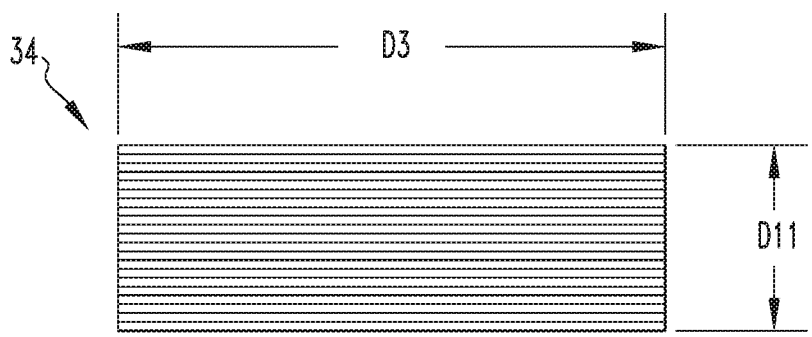

FIGS. 10A and 10B show operation of personal care appliance 2 in another alternative mode of operation. As shown in FIGS. 10A and 10B, the control electronics of main circuit board 20 control motor 26 such that when a first half cycle (e.g., the positive half cycle) of the AC current is generated from battery 22 during each period (each complete cycle) of the AC current, it is provided to E-core member 34 (FIG. 10A) to energize/magnetize E-core member 34, and when a second, opposite half cycle (e.g., the negative half cycle) of the AC current is generated from battery 22 during each period (each complete cycle) of the AC current, it is not provided to the E-core member 34 (FIG. 10B). As a result, during each first half cycle of the AC current, E-core member 34 will have the polarities as shown in FIG. 10A, which will cause armature assembly 32 to be driven in the direction shown by the arrows in FIG. 10A. In addition, during each second, opposite half cycle of the AC current, E-core member 34 will not be energized, and as a result, armature assembly 32 will move in the direction shown by the arrows shown in FIG. 10B as a result of the natural flexing of second arm 46 of armature assembly 32 (i.e., the armature assembly 32 is not driven in this direction by motor 26). In this alternative embodiment, the present inventors have found that particularly advantageous performance can be obtained by utilizing an E-core member 34 comprising a stack of a plurality of shaped metal sheets or plates (e.g., silicon steel sheet) having the dimensions shown in FIGS. 11A and 11B (and described below) and providing at least 400 Milliamps amps of current during the first half cycle. In FIGS. 11A and 11B, the dimensions are as follows: D1 is 21 mm, D2 is 9.46 mm, D3 is 27 mm, D4 is 20 mm, D5 is 12 mm, D6 is 3.5 mm, D7 is 4.5 mm, D8 is 4 mm, D9 is 22.06 mm, D10 is 3.3 mm in diameter, and D11 is 9.2 mm.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A personal care appliance, comprising:
   a housing;
   a drive assembly provided in the housing, the drive assembly including:
     a stator;
     an armature adjacent the stator, wherein the stator, when energized, is structured to cause the armature to oscillate back and forth;
   a first mounting member secured to the housing, the first mounting member having a first hole extending through the first mounting member and forming part of a first bearing member;
   a pivot arm member including a first arm, a second arm, and a shaft member provided between the first arm and the second arm, the shaft member having a first end portion, wherein a first end of the first arm is coupled to the armature assembly and a second end of the first arm is coupled to a first side of the shaft member, wherein a first end of the second arm is coupled to a second side of the shaft member opposite the first side of the shaft member, and wherein a second end of the second arm is coupled the first mounting member, and wherein the first end portion of the shaft member is received through the first hole; and a workpiece member coupled to the first end portion of the shaft member such that oscillation of the armature causes the workpiece member to oscillate relative to the housing.

2. The personal care appliance according to claim 1, wherein a longitudinal axis of the shaft member is perpendicular to a longitudinal axis of the first arm and a longitudinal axis of the second arm.

3. The personal care appliance according to claim 1, wherein the first mounting member includes a base member having a plurality of screw cylinders extending upwardly therefrom, each of the screw cylinders being fit over and secured to a respective peg members provided as part of the housing, wherein the base member includes a mounting arm coupled to a first one or more of the screw cylinders, and wherein the second end of the second arm is coupled to the mounting arm.

4. The personal care appliance according to claim 3, further comprising a second mounting member secured to a second one or more of the screw cylinders, wherein a second end portion of the shaft member opposite the first end portion of the shaft member is received through the second mounting member.

5. The personal care appliance according to claim 1, further comprising a first elastomeric insert provided in the first hole and forming part of the first bearing member.

6. The personal care appliance according to claim 1, wherein the workpiece member is selectively attachable to and detachable from the first end portion of the shaft member.

7. The personal care appliance according to claim 1, wherein the workpiece member comprises a brush head assembly having a plurality of bristles extending therefrom.

8. The personal care appliance according to claim 1, wherein the workpiece member comprises one or more components made with an antimicrobial material that is both (i) safe for use on the skin, and (ii) resists and/or inhibits the growth of mold, mildew, fungus and/or bacteria.

9. The personal care appliance according to claim 8, wherein the workpiece member comprises a brush head assembly having a plurality of bristles extending therefrom, wherein the bristles include the antimicrobial material as an additive thereto and/or are coated with the antimicrobial material.

10. The personal care appliance according to claim 9, wherein the antimicrobial material includes silver ions.

11. The personal care appliance according to claim 9, wherein the antimicrobial material includes essential plant oils and/or essential minerals.

12. The personal care appliance according to claim 9, wherein the antimicrobial material includes a bacteria resistant polymer.

13. The personal care appliance according to claim 1, wherein the housing includes a handle portion, and wherein the handle portion is provided with a number of overlay portions structured to prevent the personal care appliance from slipping during use.

14. The personal care appliance according to claim 13, wherein the overlay portions are made of a rubber material.

15. The personal care appliance according to claim 14, wherein the overlay portions include a plurality of protruding members extending outwardly therefrom.

16. The personal care appliance according to claim 1, further comprising control electronics structured to control operation of the stator and armature such that the armature is caused to oscillate back and forth in a pulse mode wherein the armature is caused to move back and forth between a first lateral maximum position and a second lateral maximum position with a pause at each of the first lateral maximum position and the second lateral maximum position before initiating movement in an opposite direction.

17. The personal care appliance according to claim 16, wherein the pause is at least 300 milliseconds.

18. The personal care appliance according to claim 16, wherein the control electronics are structured to cause the Armature to oscillate back and forth at least one of 240 cycles/second, 220 cycles/second, and 200 cycles/second.

19. The personal care appliance according to claim 18, wherein the control electronics are structured to cause the armature to oscillate back and forth at 240 cycles/second, 220 cycles/second, and 200 cycles/second as selected by a user.

20. The personal care appliance according to claim 1, further comprising: (i) a power source for providing AC current, the AC current comprising a plurality of complete cycles, each complete cycle having a first half cycle and a second half cycle, (ii) control electronics structured to control operation of the stator and armature by providing only the first half cycle of each of the complete cycles to the stator to energize the stator and not providing any of the second half cycles of each of the complete cycles to the stator.

21. The personal care appliance according to claim 20, wherein the control electronics are structured to cause the armature to oscillate back and forth at 200 cycles/second or greater.

22. The personal care appliance according to claim 1, wherein the workpiece member includes a hexagonal female attachment member structured to receive the first end portion of the shaft member, the first end portion comprising a hexagonal male member.

* * * * *